US00RE38323E

(19) United States
(12) Reissued Patent
Sugihara et al.

(10) Patent Number: US RE38,323 E
(45) Date of Reissued Patent: Nov. 18, 2003

(54) CELL POTENTIAL MEASUREMENT APPARATUS HAVING A PLURALITY OF MICROELECTRODES

(75) Inventors: Hirokazu Sugihara, Katano (JP); Akihito Kamei, Hirakata (JP); Yasushi Kobayashi, Osazaki (JP); Makoto Taketani, Irvine, CA (US); Tadayasu Mitsumata, Hirakata (JP)

(73) Assignee: Matsushita Electric Industrial Co., Ltd., Osaka (JP)

(21) Appl. No.: 09/169,188

(22) Filed: Oct. 8, 1998

Related U.S. Patent Documents

Reissue of:
(64) Patent No.: 5,563,067
Issued: Oct. 8, 1996
Appl. No.: 08/464,116
Filed: Jun. 5, 1995

(30) Foreign Application Priority Data

Jun. 13, 1994 (JP) ..... 6-130176

(51) Int. Cl.[7] ..... C12M 1/34

(52) U.S. Cl. ..... 435/287.1; 435/288.7; 435/289.1; 435/173.1; 435/368; 204/403; 324/447; 324/692; 356/246

(58) Field of Search ..... 435/287.1, 288.7, 435/289.1, 173.1, 368; 204/403; 356/246, 56; 324/447, 692

(56) References Cited

U.S. PATENT DOCUMENTS

| | | | |
|---|---|---|---|
| 3,448,377 A | 6/1969 | Seiwatz et al. | |
| 4,072,578 A | 2/1978 | Cady et al. | 195/127 |
| 4,704,576 A | 11/1987 | Tributsch et al. | 324/158 R |
| 4,758,786 A | 7/1988 | Hafeman | 324/158 D |
| 4,855,243 A | 8/1989 | Simic-Glavaski | 436/63 |

(List continued on next page.)

FOREIGN PATENT DOCUMENTS

| | | |
|---|---|---|
| DE | 3634132 | 4/1987 |
| EP | 0300651 | 1/1989 |
| EP | 0367432 | 5/1990 |

(List continued on next page.)

OTHER PUBLICATIONS

Baxter et al., "Microfabrication in silicon microphysiometry" *Clin. Chem.* 40(9):1800–1804 (1994).

Brochure for muti channel systems, data acquisition: High end tools for multi electrode measurements–Mea 60–SYSTEM, mea 1060, multi electrode array.

(List continued on next page.)

*Primary Examiner*—David A. Redding
(74) *Attorney, Agent, or Firm*—Morrison & Foerster LLP

(57) ABSTRACT

A cell potential measurement apparatus, which uses a planar electrode enabling a multi-point simultaneous measurement of potential change arising from cell activities, is provided which can conduct measurements accurately and efficiently as well as can improve convenience of arranging measurement results. According to the configuration of the cell potential measurement apparatus of this invention, it includes an integrated cell holding instrument, which includes a planar electrode provided with a plurality of microelectrodes arranged in a matrix form on the surface of a substrate, a cell holding part for placing cells thereon, drawer patterns from the microelectrodes, and electric contact points for outside connections; an optical observation means for optical observations of cells; a stimulation signal supply means to be connected to the cell holding instrument for providing electric stimulation to the cells; and a signal processing means to be connected to the cell holding instrument for processing an output signal arising from electric physiological activities of the cells. It is preferable that a cell culturing means is also provided for maintaining a culture atmosphere of the cells placed on the integrated cell holding instrument.

28 Claims, 12 Drawing Sheets

U.S. PATENT DOCUMENTS

| | | | | |
|---|---|---|---|---|
| 4,856,073 | A | 8/1989 | Farber et al. | 382/6 |
| 4,963,815 | A | 10/1990 | Hafeman | 324/715 |
| 5,187,096 | A | 2/1993 | Giaever et al. | 435/291 |
| 5,432,086 | A | 7/1995 | Fränzl et al. | 435/291 |
| 5,563,067 | A | 10/1996 | Sugihara et al. | 435/287.1 |
| 5,810,725 | A | 9/1998 | Sugihara et al. | 600/372 |

FOREIGN PATENT DOCUMENTS

| | | |
|---|---|---|
| EP | 0585933 | 3/1994 |
| GB | 1514046 | 8/1976 |
| JP | 52-31825 | 3/1977 |
| JP | 55-84148 | 6/1980 |
| JP | 63-84476 | 4/1988 |
| JP | 3-265814 | 11/1991 |
| JP | 4-204244 | 7/1992 |
| JP | 06078889 | 3/1994 |
| JP | 06296595 | 10/1994 |
| WO | WO 90/11371 | 10/1990 |
| WO | WO 91/17240 | 11/1991 |
| WO | WO 92/15700 | 9/1992 |

OTHER PUBLICATIONS

Company brochure RS "Steckverbindungen–Labor/prüfung 1–1193".

Company brochure ARIES "Series 537 universal PLCC" and "Series 536 PLCC" (published later but relating to earlier–distributed components).

Company brochure 3M "Textool sockets and trays" (also relating to an earlier distributed component).

Eggers et al., "Electronically wired petri dish: A microfabricated interface to the biological neuronal network" *J. Vac. Sci. Technol. B.* 8(6):1392–1398 (1990).

Gähwiler et al., "Multiple actions of acetylcholine on hippocampal pyramidal cells in organotypic explant cultures" *Neurosci.* 7(5):1243–1256 (1982).

Gonzales et al., "Cell and explant culture of olfactory chemoreceptor cells" *J. Neurosci.* 14(2):77–90 (1985).

Gross et al., "A new fixed–array multi–microelectrode system designed for long–term monitoring of extracellular single unit neuronal activity in vitro" *Neurosci. Lett.* 6:101–105 (1977).

Gross et al., "Recording of spontaneous activity with photoetched microelectrode surfaces from mouse spinal neurona in culture" *J. Neurosci. Meth.* 5:13–22 (1982).

Gross et al., "Long–term monitoring of spontaneous single unit activity from neuronal monolayer networks cultured on photoetched mutielectrode surfaces" *J. Electrophysiol. Tech.* 9:55–69 (1982).

Gross et al., "Multielectrode investigations of network properties in neural monolayer cultures", In: Proc. of the sixth southern biomedical engineering conference, pp212–217, Mc Gregor abd Werner, Washington D.C., (1987).

Gross et al., "An approach to the determination of network properties in mammalian neuronal monolayer cultures" *Proc. of the First IEEE Conference on Synthetic Microstructures in Biological Res.*, Arlie, VA., Mar. 24–26, 1986.

Hämmerle et al., "Extracellular recording in neuronal networks with substrate integrated microelectrode arrays" *Biosens. Bioelect.* 9:691–696 (1994).

Hazeki et al., "Modification by Islet–activating protein of receptor–mediated regulation of cyclic AMP accumulation in isolated rat heart cells" *J. Biol. Chem.* 256(6):2856–2862 (1981).

Kuriyama et al., "A single chip biosensor" *NEC Res. Develop.*, No. 78, pp 1–5, Tokyo, JP. (1985).

Kuroda, "Adenosine/ATP receptor in nervous system and physiologic function" *Protein Nucl. Acid Enzyme* 29(12):1405–1423 (1984) English Abstract.

Nakao et al., "Scanning–laser–beam semiconductor ph–imaging sensor" *Sensors & Actuators B* 20(2/3):119–123 (1994).

Nisch et al., "A thin film microelectrode array for monitoring extracellular neuronal activity in vitro" *Biosens. Bioelect.* 9:737–741 (1994).

Novac et al., "Recording from the Aplysia abdominal ganglion with a planar microelectrode array" *IEEE Trans. Biomed. Eng. BME–33*(2):196–202 (1986).

Novak et al., "Multisite hippocampal slice recording and stimulation using a 32 element microelectrode array" *J. Neurosci. Meth.* 23:149–159 (1988).

Novak et al., "A high–speed multichannel neural data acquisition system for IBM PC compatabilities" *J. Neurosci. Meth.* 26:239–247 (1989).

Suematsu et al., "α receptor" *Protein Nucl. Acid Enzyme* 29(12):1338–1352 (1984) English Abstract.

Thomas et al., "A miniature microelectrode array to monitor the bioelectric activity of cultured cells" *Exptl. Cell Res.* 74:61–66 (1972).

Tübingen et al., "2nd CEC workshop on bioelectronics: Interfacing biology with electronics" *Biosens. Bioelect.* 9:Preface (i) (1994).

Yamamoto, "In vitro synaptic activity" *Protein Nucl. Acid Enzyme* 22(6):502–505 (1977) English Abstract.

Yamamoto et al., "Black widow spider venon: excitatory action on hippochampal neurons" *Brain Res.* 244(2):382–386 (1982).

Yamamoto, "Electrical activity of brain sector" *Protein Nucl. Acid Enzyme* 29(12):1205–1211 (1984) English Abstract.

CELL POTENTIAL MEASUREMENT APPARATUS HAVING A PLURALITY OF MICROELECTRODES

Matter enclosed in heavy brackets [ ] appears in the original patent but forms no part of this reissue specification; matter printed in italics indicates the additions made by reissue.

*Application Ser. No. 09/169,188, filed Oct. 8, 1998, and application Ser. No. 09/688,077, filed Oct. 13, 2000, are each reissues of U.S. Pat. No. 5,563,067 (Application Ser. No. 08/464,116), filed Jun. 5, 1995.*

FIELD OF THE INVENTION

This invention relates to a cell potential measurement apparatus which is used in the field of electrical neurophysiology for measuring potential change associated with activities of nerve cells or nerve organs.

BACKGROUND OF THE INVENTION

Recently, medical investigations into nerve cells and the possibility of using nerve cells as electric elements have been actively pursued. When nerve cells are active, action potential is generated. This action potential rises from a change in ion concentration inside and outside the cell membrane which is accompanied by a change in ion permeability in nerve cells and thus from the change in cell membrane potential accompanied thereby. Therefore, measuring this potential change accompanied by the ion concentration change (that is, the ion current) near the nerve cells with electrodes enables the detection of activities of nerve cells or nerve organs.

In order to measure the above-mentioned potential arising from cell activities, it is possible, for example, to insert an electrode comprising glass into an area of cells to measure extracellular potential. When evoked potential due to stimulation is measured, a metal electrode for stimulation is inserted together with a glass electrode for recording. However, measurement by the insertion of these electrodes has the possibility of damaging the cells, and measurement over a long period of time is difficult to carry out. In addition, due to restrictions of space and the need for operating accuracy, multipoint simultaneous measurements are also difficult to carry out.

Therefore, the present inventors developed a planar electrode comprising an insulation substrate and a multiplicity of microelectrodes and their drawer patterns formed thereon with the use of a conductive material, and cell culture could take place on that surface (disclosed in Laid-open Japanese patent application Nos. (Tokkai Hei) 6-78889 and 6-296595). With this planar electrode, multi-point simultaneous measurements of potential change can be carried out without being affected by restrictions of space at a plurality of points with a short electrode-to-electrode distance. Also, this electrode enabled long-term measurement.

However, a measurement apparatus which can efficiently use this kind of planar electrode, conduct measurements accurately and efficiently, and improve the arranging of measurement results has been strongly desired. Therefore, it is an object of this invention to provide a cell potential measurement apparatus which is capable of accomplishing these needs in the art.

SUMMARY OF THE INVENTION

In order to accomplish these and other objects and advantages, a cell potential measurement apparatus of this invention comprises (A) an integrated cell holding instrument provided with a plurality of microelectrodes on a substrate, a cell holding part for placing cells thereon, and an electric connection means for providing an electric signal to the microelectrodes and for leading out an electric signal from the microelectrodes; (B) a stimulation signal supply means to be connected to the electric connection means of the cell holding instrument for providing electric stimulation to the cells; and (C) a signal processing means to be connected to the electric connection means of the cell holding instrument for processing an output signal arising from electric physiological activities of the cells.

It is preferable that the cell potential measurement apparatus of this invention further comprises an optical observation means for observing the cells optically. It is also preferable that the cell potential measurement apparatus of this invention further comprises a cell culturing means for maintaining an environment for culture of cells which are placed on the integrated cell holding instrument. This configuration enables measurement over a long period of time.

Generally, the measurement conducted by means of the above-configured apparatus of this invention is carried out, for example, in the following steps. Sample cells are placed in a cell holding part of an integrated cell holding instrument, and a plurality of microelectrodes contact the cells.

An image of the cells is obtained by an optical observation means. A stimulation signal is applied between a pair of electrodes selected optionally from the plurality of microelectrodes by a stimulation signal supply means via an electric connection means. A change of evoked potential over time which is obtained in each of the other electrodes is provided to a signal processing means via the electric connection means, which is then output, for example, to a display device etc. after going through the necessary signal processing. The measurement of spontaneous potential which is not provided with a stimulation signal is carried out in a similar way.

The above-mentioned electric chemical measurement of cells must be conducted in a condition in which the cells are alive. Therefore, it is common to use cultured cells, and the cell holding part of the integrated cell holding instrument can be equipped with a culture medium. Since the integrated cell holding instrument is detachable from the measurement apparatus, each integrated cell holding instrument can be placed inside an ordinary incubator for cell culture and then taken out from the incubator and placed in the measurement apparatus. When a cell culturing means is further provided to maintain an environment for culture of the cells on the integrated cell holding instrument, long-term measurement is enabled. This cell culturing means comprises a temperature adjustment means for maintaining a constant temperature, a means for circulating a culture solution, and a means for supplying a mixed gas of air and carbon dioxide (e.g., $CO_2$ 5%).

It is preferable that the integrated cell holding instrument comprises a plurality of microelectrodes arranged in a matrix form (latticed) on the surface of a glass plate, conductive patterns for drawing these microelectrodes, electric contact points which are connected to edge parts of these conductive patterns, and a coating of insulation covering the surface of these conductive patterns, and the cell holding part is disposed in an area including the plurality of microelectrodes.

The use of a transparent glass plate as the substrate faciliates optical observations of the cells. Therefore, it is preferable that the conductive patterns or the insulation coating are also substantially transparent or translucent. Furthermore, when the plurality of microelectrodes is arranged in a matrix form, it is easier to specify positions of electrodes which are applied with stimulation signals or electrodes where voltage signals arising from cell activities are detected. For example, it is preferable to arrange 64 microelectrodes in 8 columns and 8 rows. In addition, the surface area of each electrode should be as broad as possible for reducing surface resistance and enhancing detection sensitivity. However, taking restrictions etc. arising from an electrode-to-electrode distance and space resolution of measurement into consideration, it is preferable that each electrode has a surface area of from $4\times10^2$ $\mu m^2$ to $4\times10^4$ $\mu m^2$.

Furthermore, it is preferable that the electric connection means includes a half-split holder which has a contact touching the electric contact point and fixes the glass plate by holding it from the top and bottom. According to this configuration, fixation of the glass plate and drawing of the microelectrodes to the outside can be performed easily and accurately. Furthermore, it is preferable that the electric connection means not only fixes the holder, but also comprises a printed circuit board having an outside connection pattern which is connected to the contact of the holder via a connector. As a result, connection with outside instruments, namely, with a stimulation signal supply means and a signal processing means is facilitated. For the transmission of stimulation signals or detection signals with as little attenuation and distortion as possible, contact resistance of the electric contact point with the contact as well as contact resistance of the contact with the connector are both preferably below 30 m ohm.

In addition, it is preferable that the optical observation means comprises an optical microscope, and an image pick-up device and an image display device connected to the optical microscope. In other words, the image of cells which is enlarged by a microscope is picked up by an image pick-up device (e.g., video camera) and then displayed in an image display device (e.g., a high-accuracy display), so that it is easier to conduct measurement while observing the cells and the electrode position. More preferably, when the optical observation means is further comprised of an image storage device, it is possible to record measurement results.

Also, when a pulse signal generator is used as the stimulation signal supply means, various kinds of signal waveforms can be applied as stimulation signals to the cells. It is preferable that the signal processing means comprises a multi-channel amplifier which amplifies a detection signal arising from cell activities and a multi-channel display device which displays an amplified signal waveform in real-time, and that signal waveforms (change of cell potential over time) obtained from a plurality of electrodes can be displayed simultaneously.

It is preferable that a computer is provided to output the stimulation signal via a D/A converter, and at the same time, to receive and process an output signal arising from electric physiological activities of the cells via an A/D converter. As a result, the stimulation signal can be determined as an optional waveform on the screen or a waveform of a detection signal can be displayed on the screen. In addition to these operations, it is easier to display these signals after being processed in various forms or to output them to a plotter or to store them. Furthermore, with the use of this computer, the optical observation means and the cell culturing means can be controlled.

DETAILED DESCRIPTION OF THE INVENTION

This invention will now be described in detail by referring to the attached figures and the following examples. The examples are illustrative and should not be construed as limiting the invention in any way.

Figure 1:
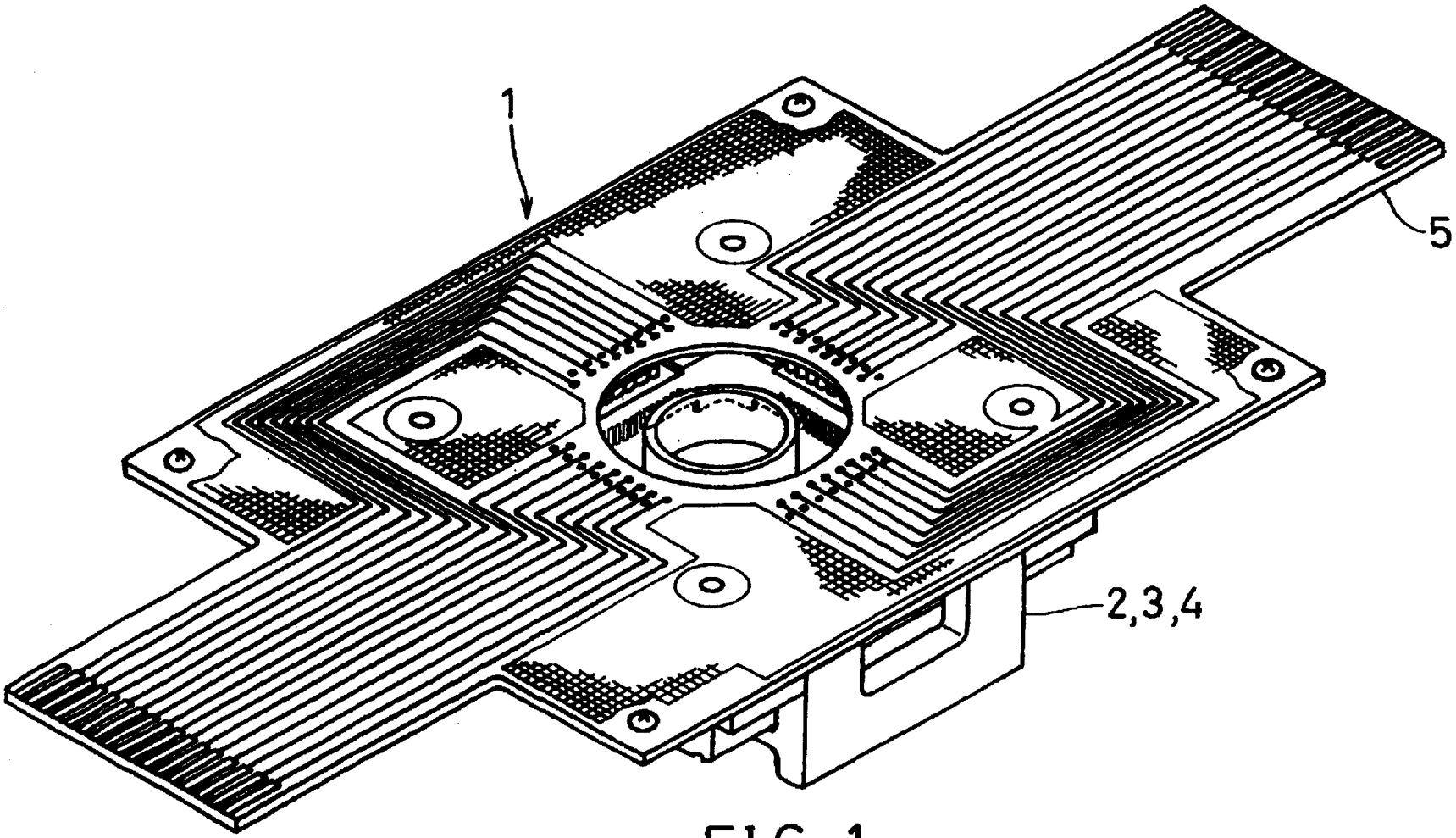
FIG. 1 is a perspective view showing an integrated cell holding instrument used for a cell potential measurement apparatus in one embodiment of this invention.

First, an integrated cell holding instrument used for a cell potential measurement apparatus of this invention will be explained. The integrated cell holding instrument 1, as shown as a perspective view in FIG. 1 and as an assembly diagram in FIG. 2, comprises a planar electrode 2, which is disposed with a plurality of microelectrodes and their drawer patterns on the surface of a glass plate, half-split holders 3, 4 for fixing the planar electrode 2 by holding it from the top and bottom, and a printed circuit board 5 on which these holders are fixed.

Figure 3:
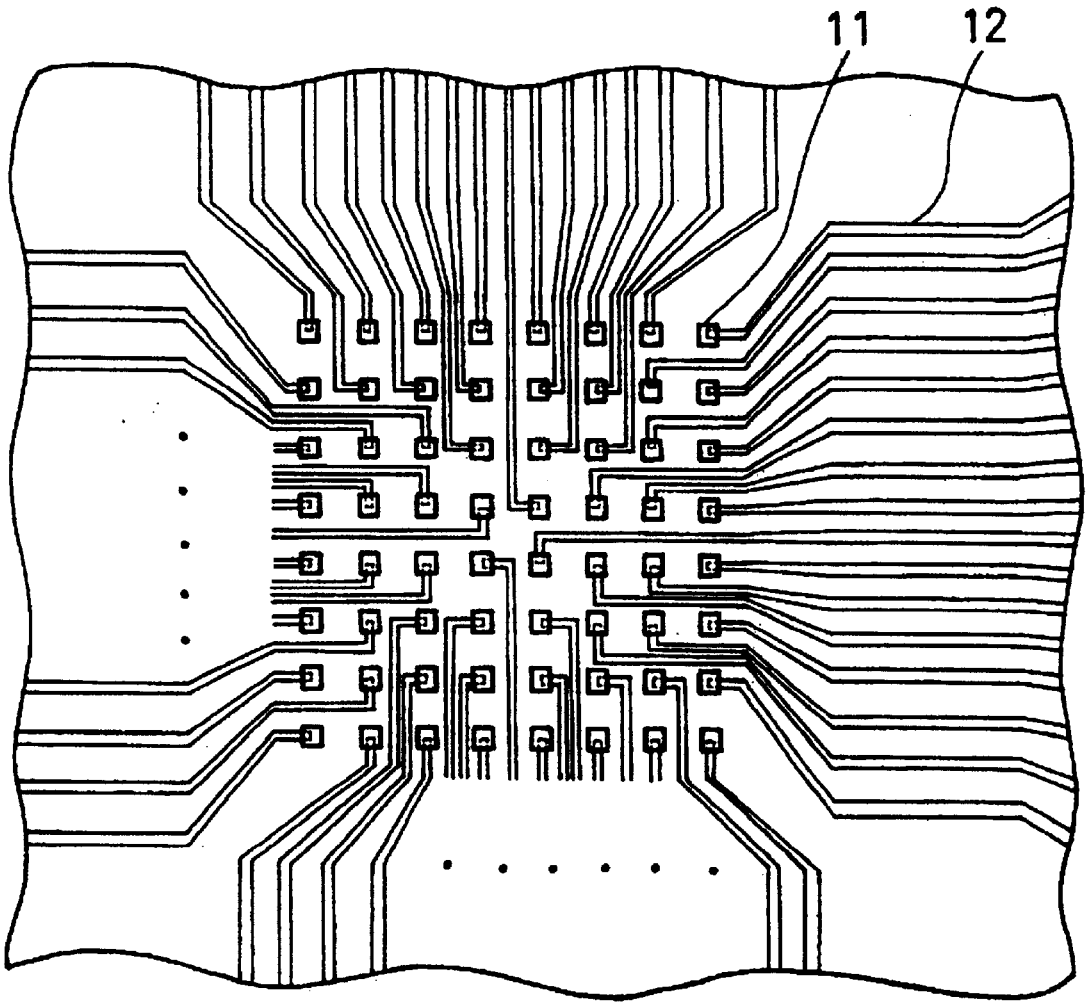
FIG. 3 is a flat diagram showing 64 microelectrodes and drawer patterns disposed on the center of a planar electrode comprising an integrated cell holding instrument.
Figure 4:
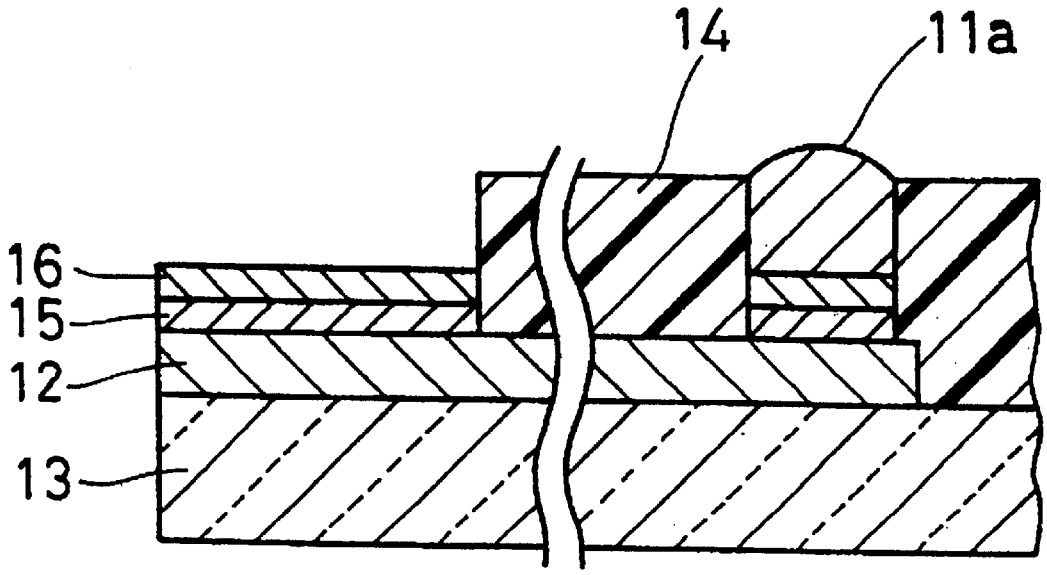
FIG. 4 is a model cross-sectional view of a planar electrode.

The planar electrode 2 is approximately the same as that disclosed in Laid-open Japanese patent application No. (Tokkai Hei) 6-78889 and others. The planar electrode 2 comprises, for example, a substrate made of a transparent pilex glass having a thickness of 1.1 mm and a size of 50×50 mm, and in the center of this substrate, 64 pieces of microelectrodes 11 are formed in a matrix form of 8×8, and each microelectrode is connected to a drawer conductive pattern 12 (cf. FIG. 3). Each of the electrodes 11 has a size of 50×50 $\mu m$ square (area $25\times10^2$ $\mu m^2$), and the center-to-center distance between the adjacent electrodes is 150 $\mu m$. Furthermore, each side of the substrate has 16 pieces of electric contact points 7 formed, totalling to 64 pieces (cf. FIG. 2). These electric contact points 7 are connected with 64 pieces of the microelectrodes 11 disposed in the center of the substrate to correspond by 1 to 1 by the drawer conductive patterns 12. 16 pieces of the electric contact points are arranged on each side with a pitch of 1.27 mm. Next, a method of manufacturing this planar electrode 2 will be explained based on its cross-sectional view shown as FIG. 4. Each part in FIG. 4 is shown on a reduced scale for convenience.

ITO (indium tin oxide), for example, was applied to form a layer of 150 nm thick on the surface of a glass plate 13, which is then formed into the conductive pattern 12 through a photoresist and etching. On top of this layer, a negative photosensitive polyimide is applied to form a layer of 1.4 $\mu$m thick, which is then formed into an insulation film 14 in a similar manner. The ITO layer is exposed at the microelectrode part, and at the part of the electric contact point, nickel 15 of 500 nm thick and gold 16 of 50 nm thick, are coated on these parts. A cylindrical polystyrene frame 6 (cf. FIG. 2) with an inner diameter 22 mm, an outer diameter 26 mm, and a height 8 mm is adhered (via a conductive pattern 8 and an insulation film 9) on the glass plate 13 using a silicone adhesive. This cylindrical polystyrene frame 6 is fixed with its center matching the center of the glass plate 13, that is, the central part of 64 microelectrodes, and the inside of the polystyrene frame 6 becomes a cell holding part. The inside of this polystyrene frame 6 is filled with solutions comprising 1 wt. % of chloroplatinic acid, 0.01 wt. % of lead acetate, and 0.0025 wt. % of hydrochloric acid. An electric current of 20 mA/cm$^2$ is generated for 1 minute to deposit platinum black 11a on the surface of the gold plating of the microelectrode part.

Figure 2:
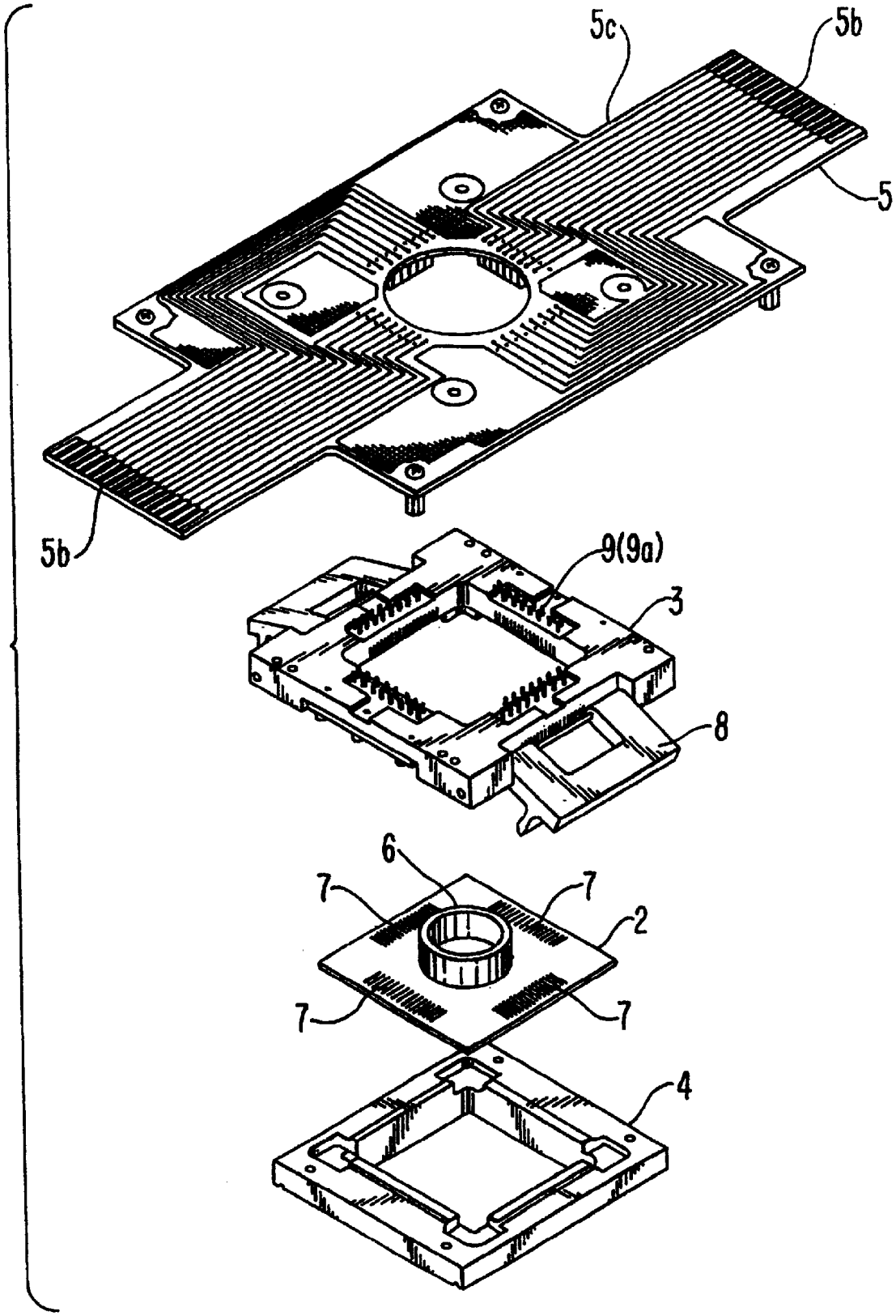
FIG. 2 is an assembly diagram of an integrated cell holding instrument.

Next, the half-split holders 3, 4 for fixing the planar electrode 2 by holding from the top and bottom will be explained. The holders 3, 4 made, for example, of resin are provided with a stage part for holding a frame part of the planar electrode 2 and with a rectangular opening in the central part, as shown in FIG. 2. The upper holder 3 is equipped with a pair of fixtures 8 and 16×4 pairs of contacts 9.

Figure 5:
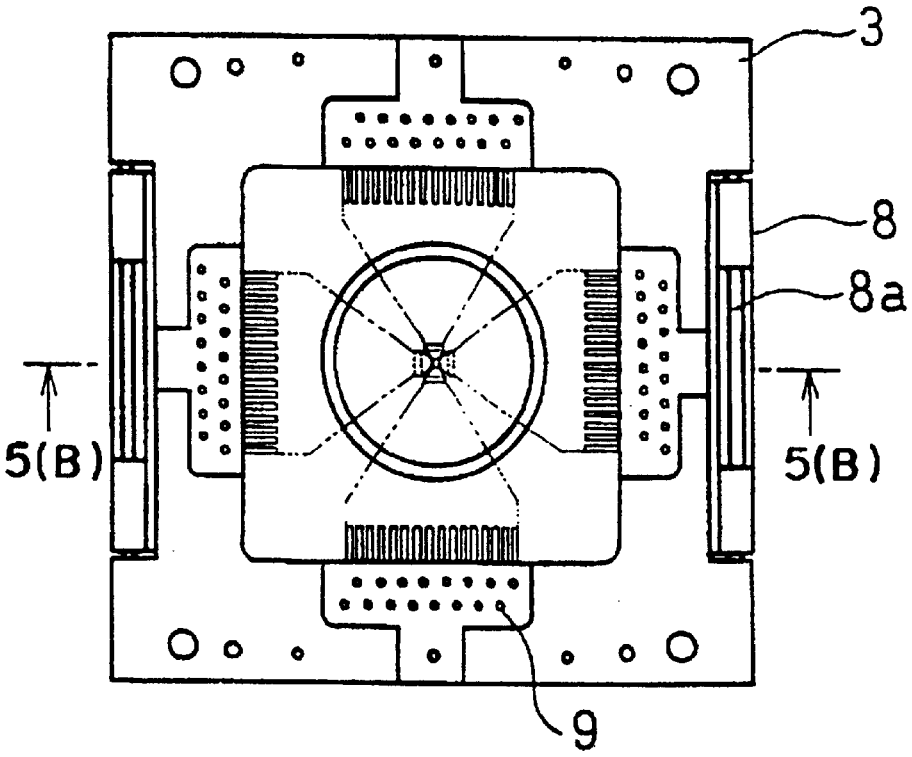
FIGS. 5(A) and 5(B) are a flat diagram and a side cross-sectional view showing a state in which a planar electrode is fixed by being held between upper and lower holders.
Figure 5:
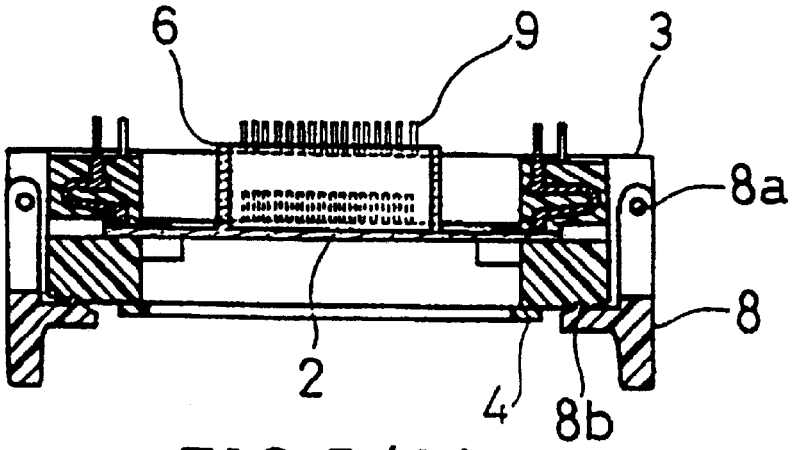
Figure 6:
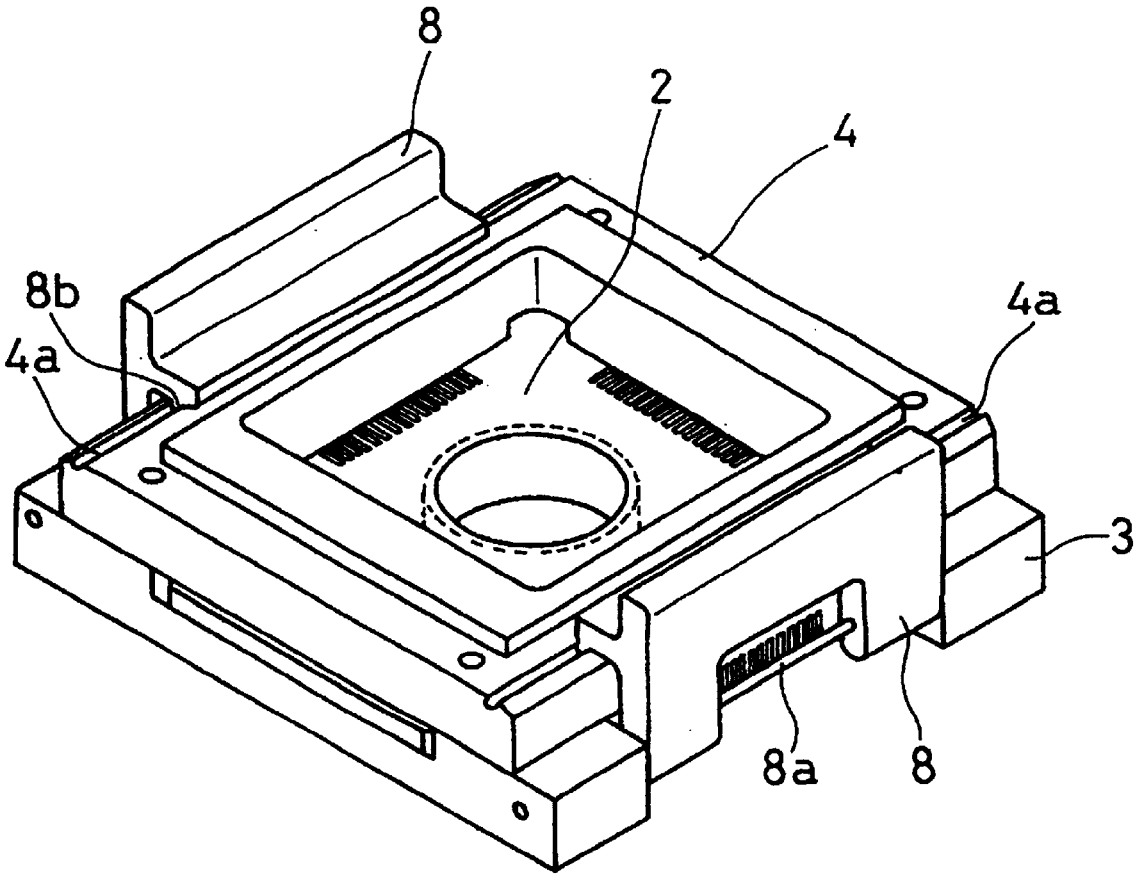
FIG. 6 is a perspective view of the planar electrode and the upper and lower holders of FIGS. 5(A) and 5(B).

A top face view of the holders 3, 4 which hold and fix the planar electrode 2 is shown in FIG. 5(A), and its side view (5(B)—5(B) cross-sectional view) is shown in FIG. 5(B), and its perspective view seen from a bottom side is shown in FIG. 6. As clearly shown in these figures, the fixture 8 is pivoted on two opposing sides of the upper holder 3 by an axis pin 8a. Furthermore, a groove 4a is formed on two opposing sides of the lower holder 4 in the bottom face. By fitting a convex part 8b of the fixture 8 into the groove 4a, the upper and the lower holders 3, 4 are firmly fixed with the planar electrode 2 held in between.

Figure 7:
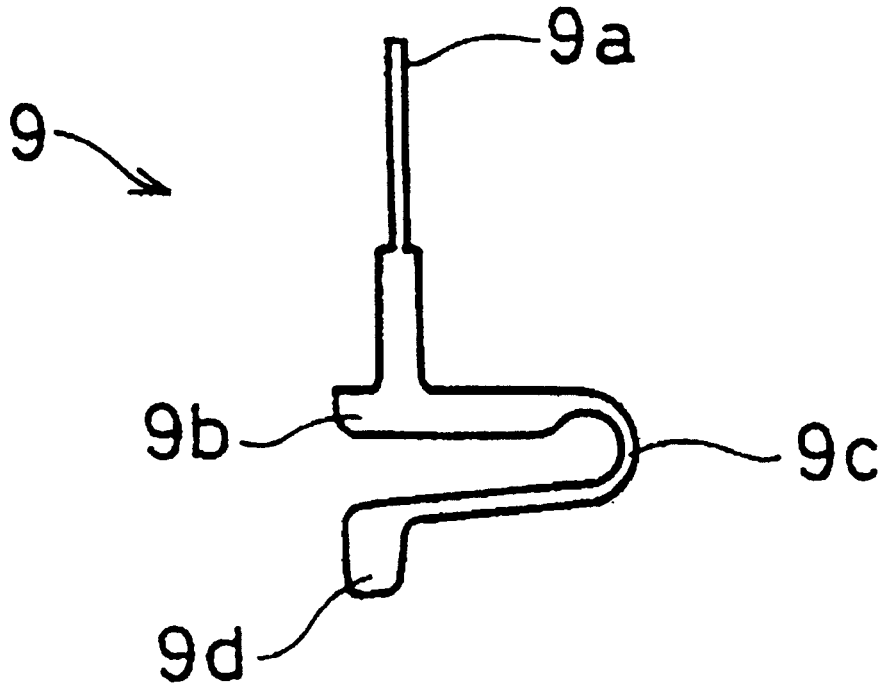
FIG. 7 is a side view of a contact equipped to an upper holder.

64 pieces of the contacts 9, which are disposed in the upper holder 3 to correspond to the electric contact points 7 of the planar electrode 2, are formed by processing an elastic, conducting metal plate such as a plate comprising BeCu coated with Ni and Au, and the contact 9 has a shape shown in FIG. 7. In other words, the contact 9 is comprised of a pin part 9a, and its base part 9b, and a movable contact part 9d extending from the base part 9b via a curved part 9c. According to this structure, the movable contact part 9d is capable of elastic displacement against the base part 9b. The upper holder 3 has 64 (16×4) pieces of holes formed which are inserted with the pin part 9a of the contact 9, and the same number of grooves are also formed which fit the base part 9b.

As shown in FIG. 2 and FIG. 5(B), the pin part 9a protrudes from the upper holder 3 at the point where the contact 9 is inserted into the above-mentioned hole and the groove and fixed. By alternately arranging the contact 9 having two different lengths of the base part 9b, 16 pieces of the pin part 9a protruding from the upper holder 3 are lined in two staggered rows. This pin part 9a is connected to a connector which is mounted on a printed circuit board 5 used for connection with the outside.

Figure 8:
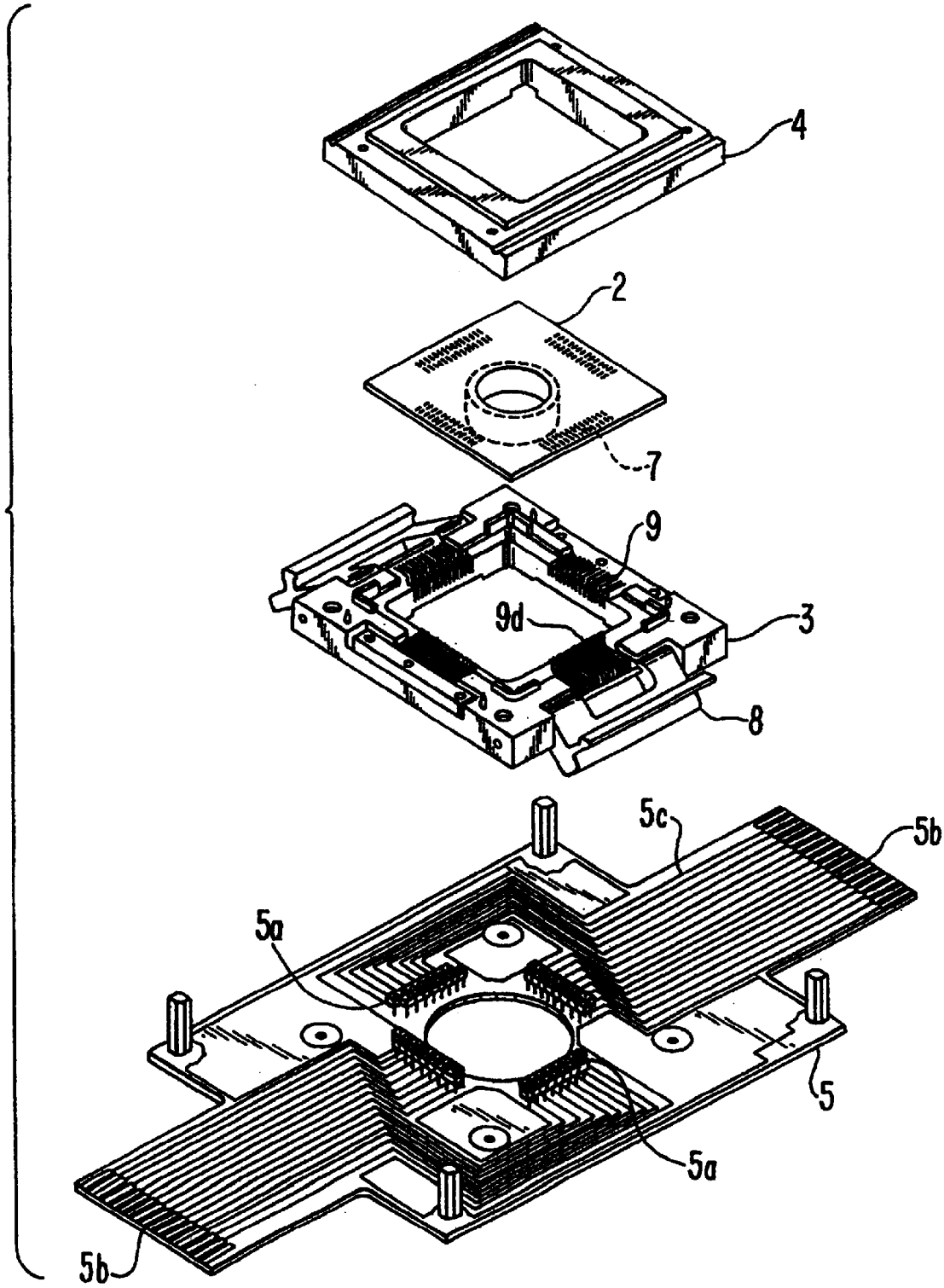
FIG. 8 is an assembly diagram of an integrated cell holding instrument seen from an opposite direction of FIG. 2.

On the other hand, the movable contact part 9d of the contact 9 protrudes from the bottom face of the upper holder 3 at the point where the contact 9 is inserted into the holder and the groove of the upper holder 3 and fixed. This arrangement is shown in FIG. 8, which is an assembly diagram seen from the side opposite the assembly diagram of FIG. 2. In this state, the planar electrode 2 is fixed between the holders 3, 4, and the movable contact part 9d of each contact 9 touches the electric contact point 7 of the planar electrode 2, and a predetermined contact pressure is exerted on the contact part due to elastic deformation of the curve part 9c. In this way, the electric contact point 7, which is connected to the microelectrode 11 of the planar electrode 2 by way of the conductive pattern 12, is electrically connected with small contact resistance (less than 30 m ohm) against the contact 9.

Next, the printed circuit board 5 will be explained. This printed circuit board 5 serves not only for fixing the assemblies of the planar electrode 2 and the holders 3, 4, but also for drawing an electrical connection via a connector to the outside, starting from the microelectrode 11 of the planar electrode 2 via the conductive pattern 12 via the electric contact point 7 to the contact 9. Furthermore, this printed circuit board 5 facilitates handling procedures, for example, installation to the measurement apparatus.

This printed circuit board 5 comprises a glass epoxy substrate disposed with double-faced patterns, and on the back face shown in FIG. 8, a connector 5a is disposed at four parts surrounding a circular opening formed in the center. By inserting 16 pieces of the pin part 9a which are protruding in two staggered rows from the four surface parts of the upper holder 3 into each corresponding connector 5a, the assemblies of the planar electrode 2 and the holders 3, 4 are fixed at the printed circuit board 5, and at the same time, they are connected electrically.

At an edge part 5b on both sides of the printed circuit board 5, electric contact points are formed at 2.54 mm pitch used for a double-faced connector edge, and these electric contact points and the connectors 5a in the central part are connected by a drawer pattern 5c. An inner row of the double-sided connector 5a is drawn by a surface pattern, whereas an outer row is drawn by a back side pattern, and each of the edge part 5b is provided with 32 electric contact points formed for both sides together, totalling 64 electric contact points. For the purpose of assuring mechanical fixation, the upper holder 3 can be fixed to the printed circuit board 5 using a vise.

Figure 9:
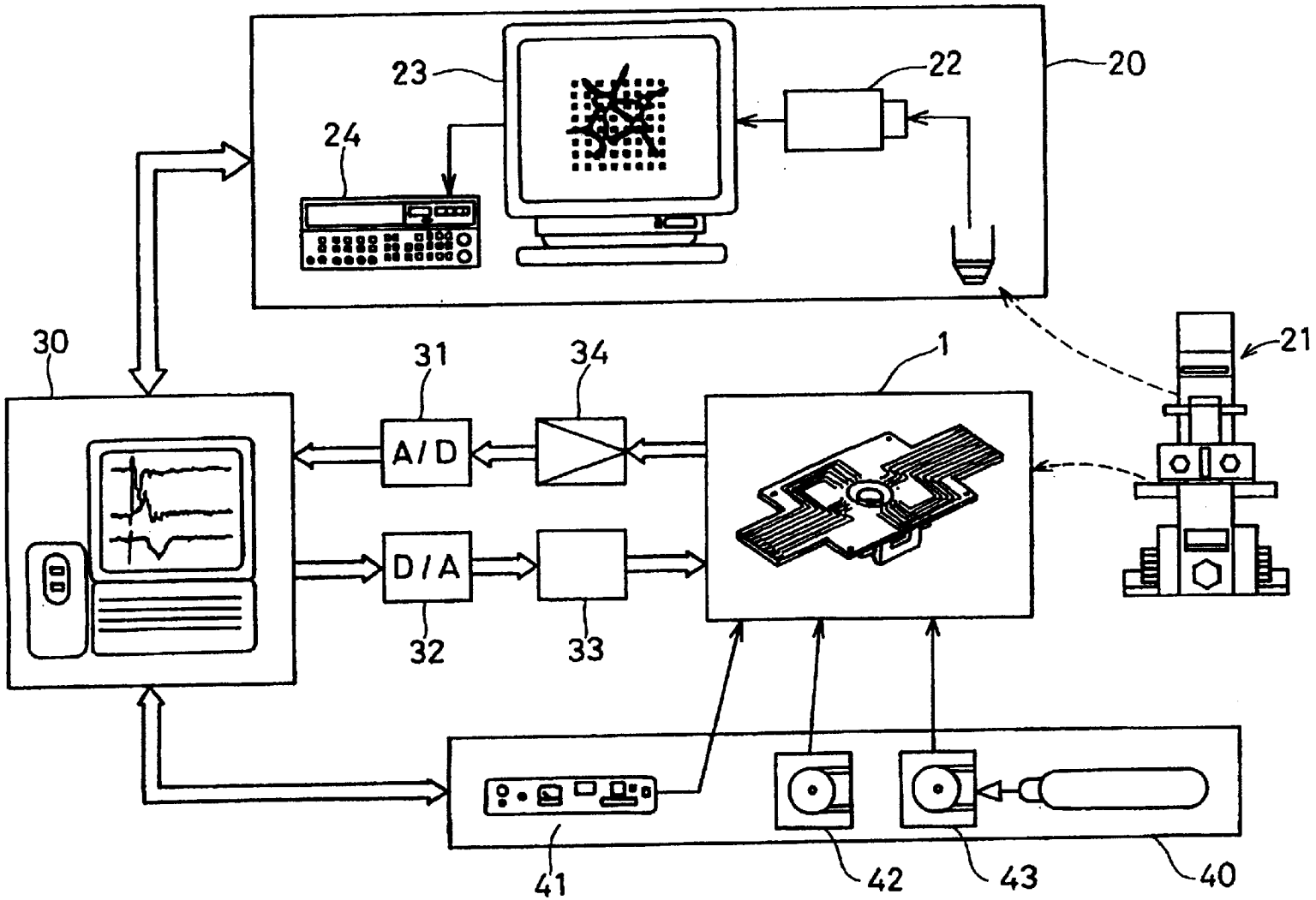
FIG. 9 is a block diagram of a cell potential measurement apparatus in one embodiment of this invention.

A preferable configuration of a cell potential measurement apparatus using the above-configured integrated cell holding instrument 1 is shown in FIG. 9. The measurement apparatus of this embodiment comprises the above-mentioned integrated cell holding instrument 1, an optical observation means 20 including an inverted microscope 21 for optical observations of cells which are placed in this integrated cell holding instrument 1, a computer 30 including a means of providing a stimulation signal to the cells and a means of processing an output signal from the cells, and a cell culturing means 40 for maintaining a suitable culture medium for the cells.

Besides the inverted microscope 21 (for example, "IMT-2-F" or "IX70" manufactured by OLYMPUS OPTICAL CO., LTD.) where the integrated cell holding instrument 1 is installed, the optical observation means 20 also includes a SIT camera 22 used for a microscope (for example, "C2400-08" manufactured by HAMAMATSU PHOTONICS K.K.), a high-accurate display 23, and an image filing device 24 (for example, "TQ-2600" or "FTQ-3100" manufactured by MATSUSHITA ELECTRIC INDUSTRIAL CO., LTD.). A SIT camera is a general term used for cameras which apply a static induction transistor to an image pickup tube, and a SIT camera is a representative example of sensitive cameras. However, the high-accuracy display 23 can be used also as a display for the computer 30. The specific devices described above in parenthesis are illustrative examples, and the invention is not limited to these devices only. This is also the same with the examples shown in the following.

As for the computer 30, a personal computer (for example, compatible with WINDOWS) is used which is mounted with an A/D conversion board and software for measurement. The A/D conversion board includes an A/D converter 31 and a D/A converter 32 shown in FIG. 9. The A/D converter 31 has 16 bits and 64 channels, and the D/A converter 32 has 16 bits and 8 channels.

The measuring software includes software for determining conditions needed for providing a stimulation signal or recording conditions of an obtained detection signal. With the use of this type of software, the computer 30 is not only capable of structuring the means of providing a stimulation signal to the cells and the means of processing the detection signal from the cells, but also is capable of controlling the optical observation means (the SIT camera and the image filing device) or the cell culturing means.

In the following, particularly useful specifications for the software for measurement will be explained. On a computer screen directed to parameter setting, it is possible to determine complicated stimulation conditions by drawing a stimulation waveform on the screen using a keyboard or a mouse. Furthermore, recording conditions are determined such that 64 input channels, a sampling rate of 10 kHz, and continuous recording over several hours are enabled. In addition, the electrode which provides a stimulation signal or the electrode which draws out a detection signal from the cells can be specified by pointing to a microscope image displayed on the screen with a mouse or a pen. Besides, various conditions such as temperature or pH of the cell culturing means 40 can be determined by using a keyboard.

A recording screen displays a spontaneous action potential or an evoked potential detected from the cells in real-time at a maximum of 64 channels. Furthermore, the recorded spontaneous action potential or the evoked potential can be displayed on top of a microscope image of cells. When the evoked potential is measured, the whole recording waveform is displayed. When the spontaneous action potential is measured, the recording waveform is displayed only when an occurrence of spontaneous action is detected by a spike detection function using a window discriminator or a waveform discriminator. When the recording waveform is displayed, measurement parameters (e.g., stimulation conditions, recording conditions, temperature, pH) at the time of recording are simultaneously displayed in real-time. There is also an alarm function provided in case when a temperature or pH goes beyond permissive limits.

On a computer screen for data analysis, FFT analysis, coherence analysis, and correlation analysis can be conducted. In addition, this screen has other functions, such as a single spike separation function using a waveform discriminator, a temporal profile display function, a topography display function, an electric current source density analysis function. Results of these analyses can be displayed on top of the microscope image stored in the image filing device.

When a stimulation signal is output from the above-configured computer 30, this stimulation signal is forwarded by way of the D/A converter 32 and an isolator 33 (for example, "BSI-2" manufactured by BAK ELECTRONICS CO., LTD.) to the cells. In other words, the stimulation signal is applied between two points selected from 64 pieces of the microelectrodes 11 in the integrated cell holding instrument 1. Then, an evoked potential arising between each of the microelectrodes 11 and a GND level (potential of culture solution) is input to the computer 30 via 64 channels of a sensitized amplifier 34 (for example, "AB-610J" manufactured by NIHON KODEN CO., LTD.) and the A/D converter 31. The amplification factor of the amplifier 34 was 100 dB, and the frequency band was from 0 to 10 kHz. However, when an evoked potential by a stimulation signal is measured, the frequency band was determined to be from 100 Hz to 10 kHz using a low cut filter.

Next, the cell culturing means 40 is provided with a temperature adjuster 41, a circulation means of culture solution 42, and a means for supplying a mixed gas of air and carbon dioxide 43. Actually, the cell culturing means 40 can be comprised of a product equivalent to a microincubator such as "PDMI-2" and a product equivalent to a temperature controller such as "TC-202" (both products manufactured by MEDICAL SYSTEMS CO., LTD.), and a $CO_2$ bomb, for example, is used. This microincubator can control the temperature in the range of 0° to 50° C. by a Peltier element, and this microincubator is capable of handing a liquid delivery speed of below 3.0 ml/min and an air supply speed of below 1.01/min. Alternatively, a microincubator integrated with a temperature controller (for example, "IMT2IBSV" manufactured by OLYMPUS OPTICAL CO., LTD.) may be used.

A preferable embodiment of the cell potential measurement apparatus of this invention was explained above. However, the cell potential measurement apparatus of this invention is not limited to this embodiment only and can be performed, for example, in various other forms described in the following.

Although a means for providing a stimulation signal to cells was comprised of a computer and a D/A converter in the above-mentioned embodiment, this means may be comprised of a general purpose or a special purpose pulse signal generator. Here, the stimulation signal is preferably determined as a bipolar constant voltage pulse comprising a pair of positive and negative pulses for eliminating artifact, that is, for preventing DC components from flowing. In addition, it is preferable to convert it to a constant electric current pulse for preventing the electric current from flowing excessively. For example, the stimulation signal is preferably comprised of a positive pulse with a pulse width of 100 $\mu$sec, an interval of 100 $\mu$sec, and a negative pulse of 100 $\mu$sec, and it is preferable that the peak electric current of the positive-negative pulse is in the range of 30 to 200 $\mu$A.

Furthermore, the installation of the cell culturing means 40 in the measurement apparatus enables continuous measurement over a long period of time. Alternatively, it is also possible to configure the apparatus such that sample cells are placed in an integrated cell holding instrument and cultured inside an incubator which is prepared separately from the measurement apparatus, and such that the integrated cell holding instrument is taken out only for a comparatively short-term measurement from the incubator to be installed in the measuring apparatus. In this case, the cell culturing means 40 is not necessarily provided in the measurement apparatus.

By using the above-mentioned cell potential measurement apparatus, nerve cells or organs were actually cultured on the integrated cell holding instrument and the potential change accompanied by activities of the nerve cells or nerve organs were measured. An example of this measurement will be explained hereafter. A cerebral cortex section of rats were used as the nerve organs, which were cultured according to a method which will be described later on in an embodiment.

It will be first referred to results of comparing a voltage waveform measured by means of an integrated cell holding instrument of this invention and a voltage waveform measured by means of a conventional general purpose glass electrode (electrode used for measurement of extracellular potential). Nerve organs which were cultured for 14 days were used as the sample. A stimulation signal was applied between two adjacent electrodes of a planar electrode comprising the integrated cell holding instrument, and a waveform of evoked potential change over time which was induced at 8 electrodes close to the two electrodes was measured. For the purpose of comparison, glass electrodes were sequentially transferred to the vicinity of the above-mentioned eight electrodes by using a three-dimensional micromanipulator, and the same voltage waveform was measured.

Figure 10:
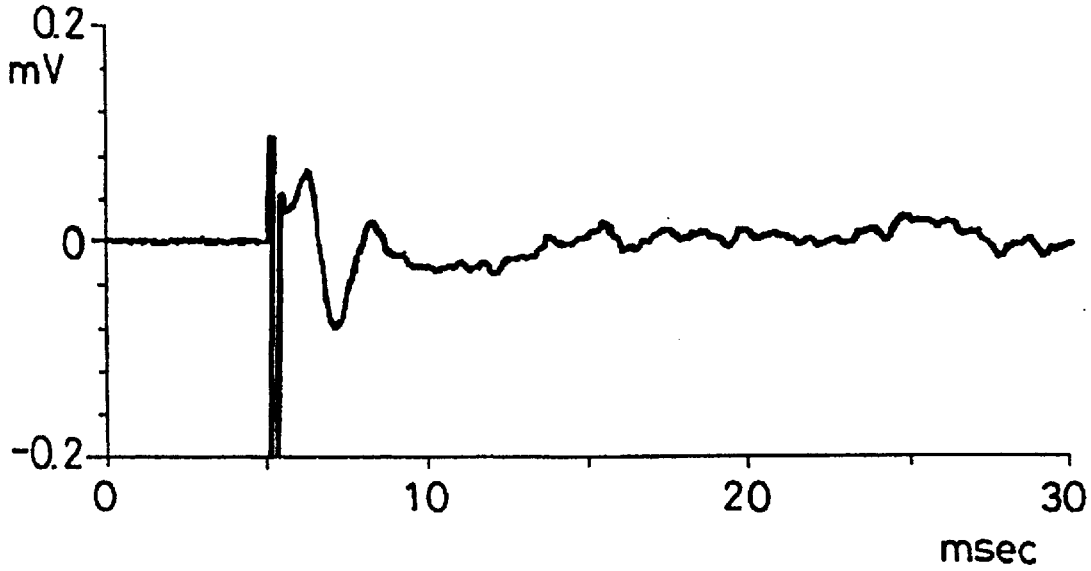
FIGS. 10(A) and 10(B) are graphs showing one comparative example of a voltage waveform arising from activities of cultured cells measured by means of an integrated cell holding instrument used in this invention and a voltage waveform measured by means of a conventional general purpose glass electrode (electrode for measurement of extracellular potential).
Figure 10B:
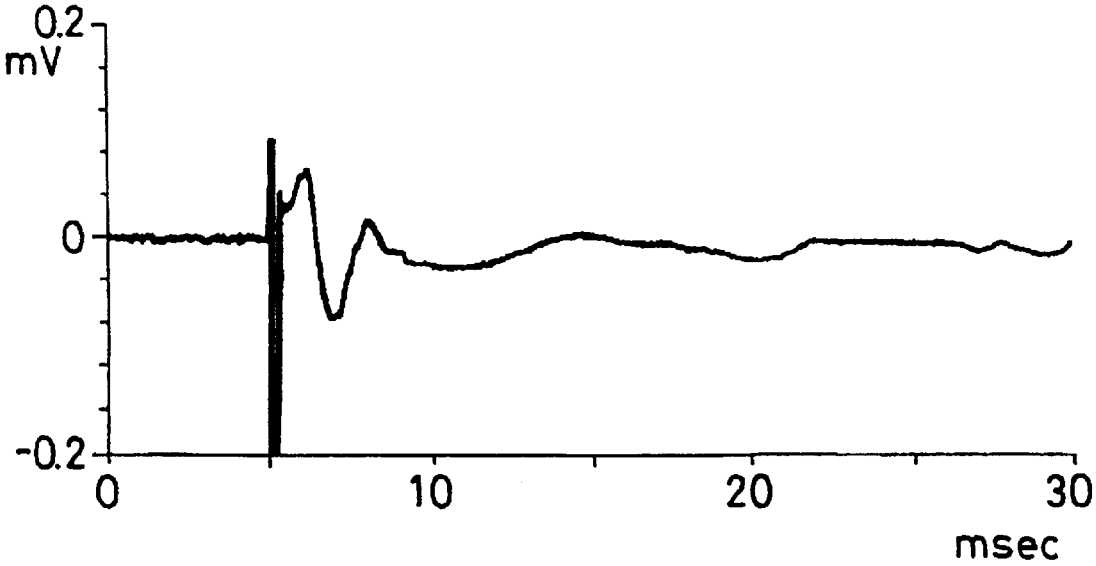

As a result of comparing the voltage waveform measured by using a planar electrode (integrated cell holding instrument) and the waveform measured by using the glass electrode at eight parts, it was clear that both waveforms were very similar at all the parts. Representative examples of these waveforms are shown in FIG. 10(A) and FIG. 10(B). FIG. 10(A) shows a waveform measured by a planar electrode, and FIG. 10(B) shows a waveform measured by a glass electrode. When both waveforms are compared, it is clear that there is a slight difference in frequency characteristics. Compared with the measurement using a planar electrode, the measurement using a glass electrode shows a small damage sustained to the follow-up property toward a rapid potential change. This is considered to result from a capacitance difference of a glass electrode and a planar electrode.

Next, an experiment was conducted to examine the relationship between progressive days of nerve organs cultured on an integrated cell holding instrument and the potential distribution arising from cell activities. Prior to culture of the cells, the surface of a planar electrode was covered with collagen gel for the purpose of enhancing the adhesive property of each electrode in the planar electrode with the cells. In other words, collagen gel with a thickness of less than 50 $\mu$m was formed on the surface of each electrode coated with platinum black and also on the surface of an insulation coating in the vicinity thereof as mentioned above. Then, on top of the collagen gel, and also where a microelectrode is present, a section of cerebral cortex of rats (thickness of less than 500 $\mu$m) was placed and cultured. Measurement results of the spontaneous potential are shown in FIGS. 11(A) to 11(C), and measurement results of the evoked potential at the time when a stimulation signal is provided are shown in FIG. 12.

Figures 11A, 11B, 11C:
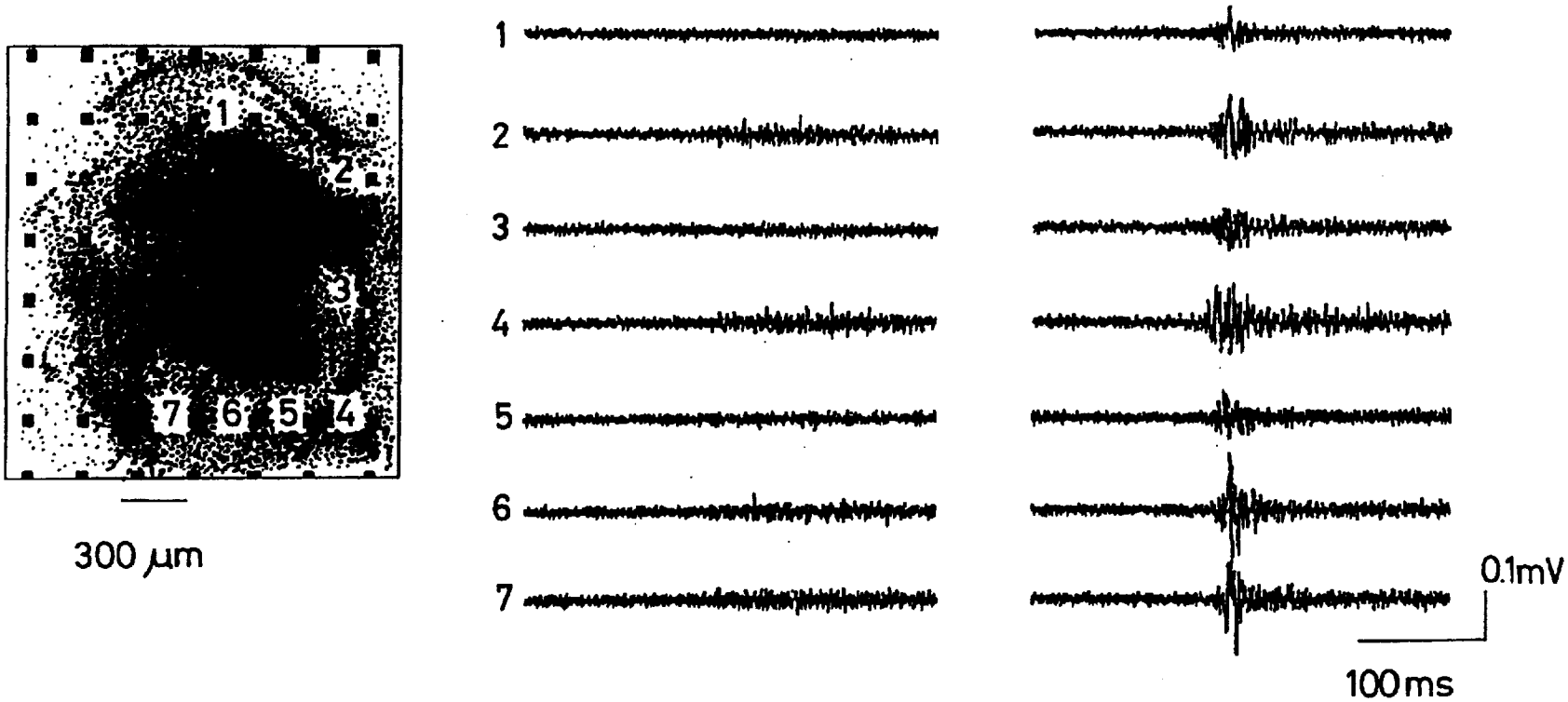
FIGS. 11(A) to 11(C) are diagrams showing measurement results of spontaneous potential of cultured cells measured by using an apparatus of this invention.
Figure 12:
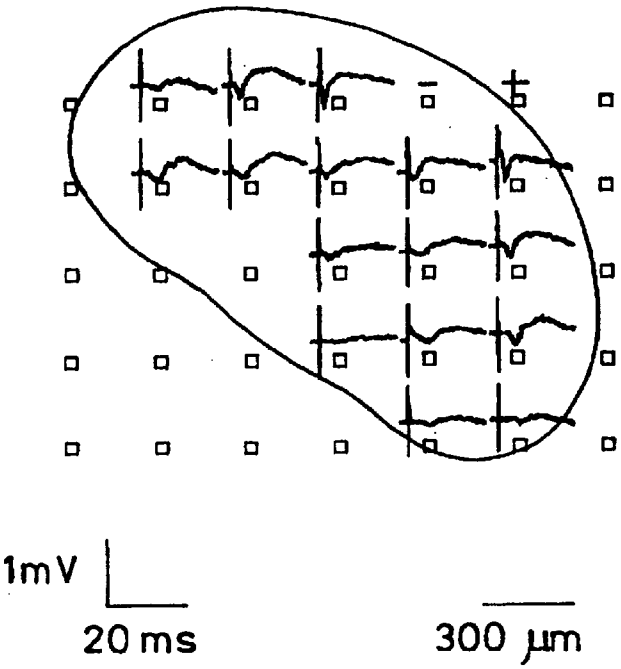
FIGS. 12(A) to 12(C) are diagrams showing measurement results of evoked potential of cultured cells measured by using an apparatus of this invention.
Figure 12:
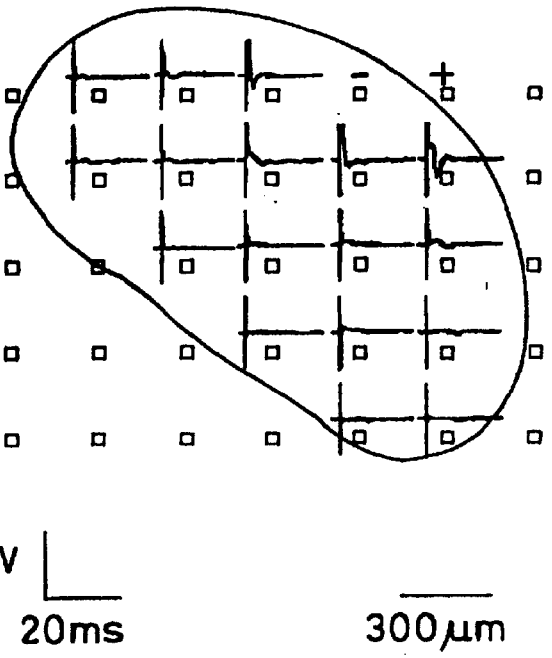
Figure 12:
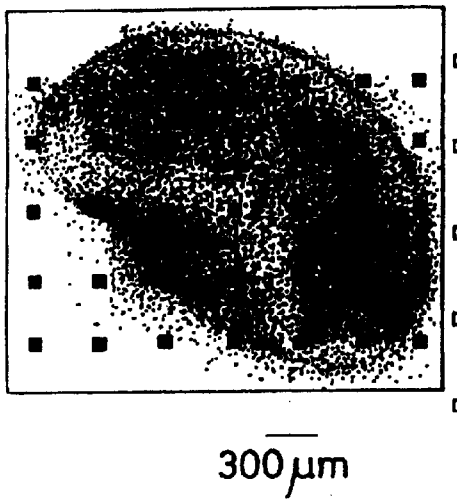

FIG. 11(A) shows a microscopic image of the sample cells and the microelectrodes, and waveforms of the spontaneous potential measured at seven electrode parts indicated as 1 to 7 on this image are shown in FIG. 1(B) and FIG. 1(C). FIG. 11(B) is a waveform measured on the sixth day after culture, and FIG. 11(C) is a waveform measured on the tenth day after culture. A scale of the microscopic image, time of the measurement waveforms, and a scale of the voltage are indicated in the figure. According to the measurement results, it is confirmed, for example, that on the sixth day after culture, the spontaneous activities of the cells measured at each electrode are weak, and synchronic property of electrodes to each other can be hardly observed, whereas on the tenth day after culture, a large number of nerve cells become active simultaneously, indicating that the synchronic property of electrodes to each other increased.

FIG. 12(A) also shows a microscopic view of the sample cells and the microelectrodes. Image processing, which is included in the software for measurement in the above-mentioned computer, was applied to draw an outline of the cells and positions of each electrode from the microscopic image onto the screen. Furthermore, the voltage waveform measured at each electrode was displayed thereon, as shown in FIG. 12(B) and FIG. 12(C). FIG. 12(B) shows a distribution of the evoked potential on the fifth day after culture, and FIG. 12(C) shows the same on the tenth day after culture. A pair of electrodes indicated on the upper right side with a + and − sign are electrodes applied with a stimulation signal. Right above a small square sign showing the position of each electrode, a waveform measured by this electrode is displayed. In these waveforms, a part where a large vertical swing is observed on the left end is an artifact corresponding directly to the stimulation signal, and the potential change after the artifact indicates actual cell activities. As a result of these measurements, it is confirmed, for example, that on the fifth day after culture, the cell activities are limited in a place which is comparatively close to the electrode positions applied with the stimulation signal, but on the tenth day after culture, the cell activities can be observed in a wide range and their scale (amplitude) becomes larger.

Next, examples of a suitable culture method for cerebral cortex slices will be explained.

1) Culture medium

The following additives were added to a culture medium in which Dulbecco modified Eagle's medium and HamF-12 medium were mixed in a volume ratio of 1:1 (media manufactured by GIBCO CO., LTD. 430-2500EB).

* glucose, GIBCO CO., LTD. 820-5023IN, 2.85 mg/L (totalling to 6 mg/L together with glucose contained originally in the above-mentioned culture medium)
* putrescine, SIGMA CO., LTD. P5780, 100 $\mu$M
* progesterone, SIGMA CO., LTD. P8783, 20 nM
* hydrocortisone, SIGMA CO., LTD. H0888, 20 nM
* sodium selenite, WAKO CO., LTD. 198-0319, 20 nM
* insulin, SIGMA CO., LTD. 16634, 5 mg/L
* transferrin, SIGMA CO., LTD. T147, 100 mg/L
* sodium bicarbonate, CO., LTD. 2.438 g/L
* addition of a suitable amount of 1N HCl or 1N NaOH to adjust to pH 7.4

After the above-mentioned additives were added, filtration and sterilization were conducted, and the culture medium was perserved at 4° C. and ready to be used. This culture medium is hereinafter simply called "culture medium"

2) Structure of a well on a planar electrode

For the convenience of culturing nerve cells or nerve organs on a planar electrode, a polystyrene cylinder having an inner diameter 22 mm, an outer diameter 26 mm, and a height 8 mm was adhered in the following steps.

(a) On the bottom face of a polystyrene cylinder (inner diameter 22 mm, outer diameter 26 mm, height 8 mm), a sufficient amount of an one-liquid silicon adhesive (DOW CORNING CO., LTD. 891 or SHIN-ETSU CHEMICAL CO., LTD. KE-42RTV) was applied.

(b) The center of a glass substrate in the planar electrode and the center of the polystyrene cylinder were carefully matched and then adhered in this state.

(c) By leaving it in an environment in which dust hardly enters for 24 hours, the adhesive was solidified.

(d) After dipping in 70% ethanol for 5 minutes, sterilization was conducted by air-drying inside a clean bench, which is then ready for processing the electrode surface.

3) Processing of the electrode surface

In order to enhance cell adhesive property on the surface of a planar electrode, collagen gel was formed on the surface of the electrode by the following method. All of these operations were conducted under a sterilized atmosphere.

(a) Solutions A, B, and C were prepared and iced.

A 0.3 vol. % diluted hydrochloric acid collagen solution (pH 3.0, NITTA GELATIN CO., LTD. Cellmatrix Type I-A)

B. Solution comprising a mixture medium of Dulbecco modified Eagle's medium and HamF-12 medium mixed in a volume ratio of 1:1 (GIBCO CO., LTD. 430-2500EB), which is not provided with sodium bicarbonate and is made with a concentration 10 times higher than for an ordinary use, and then filtration and sterilization were conducted thereto.

C. 2.2 g of sodium bicarbonate and 4.77 g of HEPES (manufactured by GIBCO CO., LTD. 845-1344 IM) were dissolved in 100 mL of 0.05N sodium hydroxide solution, and filtration and sterilization were conducted thereto.

(b) While cooling, the solutions A, B, and C were mixed at a volumn ratio of 8:1:1:. At this time, A and B are first mixed thoroughly and C is added afterwards to be mixed.

(c) In a well of a planar electrode which was cooled in advance to about 4° C., 1 mL of the mixed solution of (b) was injected little by little. After the entire electrode surface was covered, the mixed solution was removed as much as possible with a glass Pasteur pipette. Through this operation, a coating of the mixed solution was formed on the electrode surface with a thickness of less than 50 $\mu$m.

(d) By heating the planar electrode disposed with the mixed solution coating at 37° C. for 30 minutes, gelatinization of the mixed solution took place, and a collagen gel matrix was formed.

(e) 1 mL of sterilized water was added into the well of the planar electrode, and about 5 minutes thereafter, the water was removed, thereby washing.

(f) The operation of Step (e) was repeated two more times (a total of 3 times).

(g) 1 mL of the culure medium (excluding insulin and transferrin) was injected little by little into the well of the planar electrode, and preserved inside a $CO_2$ incubator under the conditions of temperature 37° C., relative humidity 97% and higher, $CO_2$ concentration 5%, and air concentration 95%, which is then ready for use.

4) Culture of nerve cells or nerve organs

Generally speaking, culture forms can be divided into two types. That is, a dissociated cell culture of nerve cells and an organotypic slice culture of a nerve organ. Each form will be explained in the following.

4-1) Dissociated culture of cerebral visual cortex nerve cells of rats

The following operations were all performed in a sterilized atmosphere.

(a) Brains of fetuses of SD rats at 16–18 days of pregnancy were removed and immersed in iced Hanks' Balanced Salt Solution (manufactured by GIBCO CO., LTD. 450-1250EB).

(b) From the brains in the iced Hanks' Balanced Salt Solution, visual cortices were cut out and transferred to minimum essential medium liquid (manufactured by GIBCO CO., LTD. 410-1100EB).

(c) In the minimum essential medium liquid, the visual cortices were cut into as small pieces as possible, 0.2 mm square at maximum.

(d) The visual cortices cut into small pieces were placed in test tubes for centrifugal separation, and after washing with Hanks' Balanced Salt Solution free from calcium and magnesium three times, they were dispersed in a suitable volume of the same liquid.

(e) In the test tubes for centrifugal separation of Step (d), Hanks' Balanced Salt Solution free from calcium and magnesium with trypsin dissolved at 0.25% was added to double the total volume. With gentle stirring, enzymatic processes were allowed to take place while the solution was constantly kept at 37° C. for 15 minutes.

(f) To the culture medium shown in 1) (containing additives, hereinafter abbreviated as a culture medium), 10 vol. % of fetal cow serum was added, which is then placed in the test tubes for centrifugal separation subjected to Step (e) to further double the total volume. With a glass Pasteur pipette having a reduced diameter produced by fire-polishing the tip end with a burner, gently repeating pipetting (about 20 times at maximum), the cells were unravelled.

(g) Centrifugation was carried out for 5 minutes at 9806.65 m/sec$^2$ (that is, 1000 g). Upon completion of centrifugation, the supernatant was discarded and the precipitate was suspended in the culture medium containing 5 vol. % of fetal cow serum.

(h) Step (g) was repeated two more times (a total of 3 times).

(i) The precipitate finally obtained was suspended in the culture medium containing 5 vol. % fetal cow serum, and using an erythrocytometer, the cell concentration in the suspension liquid was measured. After the measurement, using the similar culture medium, the cell concentration was adjusted to be 2 to $4\times10^6$ cells/mi.

(j) A planar electrode which was preserved in a $CO_2$ incubator after subjected to the process of above steps 1–3) was taken out, and the culture medium (free from insulin and transferrin) inside a well is removed, and 500 $\mu$L of a culture medium containing 5% of fetal cow serum was newly injected little by little. Furthermore, 100 $\mu$L of the cell suspension liquid with the cell concentration adjusted according to Step (i) was gently added and again let stand in the $CO_2$ incubator.

(k) Three days after the performance of Step (j), one half the culture medium was replaced with a new one. For the replaced medium, the culture medium not containing fetal cow serum was used. By reducing the concentration of fetal cow serum, growth of cells other than nerve cells (for example, glial cells) can be suppressed.

(l) Thereafter, half of the medium was replaced in a similar manner every 1 to 2 days.

4-2) Culture method of a cerebral cortex section of rats (a) Brains of SD rats 2 days old were removed and immersed in iced Hanks' Balanced Salt Solution containing 0.25 vol. % of D-glucose.

(b) In the iced Hanks' Balanced Salt Solution containing 0.25 vol. % of D-glucose, cerebral meninges attached on the brain are removed using a sharp-edged pincette very carefully not to damage the cerebral cortex.

(c) About 500 $\mu$m away from a callous body, a hemisphere of the cerebral cortex without the cerebral meninges was cut from the occipital lobe side to the frontal lobe side along the callous body by means of microscissors used for surgical operations of eyes.

(d) Subsequently, using the microscissors used for surgical operations of eyes, a cerebral cortex was cut out vertically to the cross-section of Step (c) with a thickness of 200 to 300 $\mu$m to create a section.

(e) The microscissors used for surgical operations of eyes are used further to adjust a size of the section to be about 1×1 mm.

(f) The planar electrode prepared in the above-mentioned "3) Processing of an electrode surface" was taken out from the $CO_2$ incubator, and the cerebral cortex section whose size was adjusted was sucked up with a pipette having a diameter of 2 mm and larger very gently not to damage the section, and then transferred into a culture well of the planar electrode.

(g) With a Pasteur pipette with the tip end fire-polished with a burner, the material was arranged on the electrode such that the layer structure of the cortex faces upward and is placed on the electrode, while being careful not to damage the cerebral cortex section.

(h) After the cerebral cortex section is placed on the planar electrode, the amount of the culture medium was adjusted so that a base of the section touched the culture medium and the top face was exposed to outside air.

(i) After adjusting the culture medium amount, the planar electrode was placed in a sterilized Petri dish, and about 5 ml of sterilized water at 37° C. was injected little by little into the Petri dish to prevent the culture medium from drying, and again let stand in the $CO_2$ incubator.

(j) Thereafter, the medium was replaced with a new one once every day while attending to the amount of culture medium. The culture medium amount was determined to be the same as in Step (h).

The invention may be embodied in other forms without departing from the spirit or essential characteristics thereof. The embodiments disclosed in this application are to be considered in all respects as illustrative and not as restrictive. The scope of the invention is indicated by the appended claims rather than by the foregoing description, and all changes which come within the meaning and range of equivalency of the claims are intended to be embraced therein.

What is claimed is:

1. A cell potential measurement apparatus for measurement of electrical physiological characteristics of cells, comprising:

(A) an integrated cell holding instrument provided with a plurality of microelectrodes arranged in a matrix form on the surface of a glass plate, *said microelectrodes each having an electrode area of* $4\times10^2$ $\mu m^2$ *to* $4\times10^4$ $\mu m^2$, conductive patterns connected to the microelectrodes, electric contact points which are connected to edge parts of these conductive patterns, an insulation coating covering the surface of said conductive patterns, said microelectrodes being in electrical connection to a cell holding part which is constructed so as to contain cells and arranged in an area including said plurality of microelectrodes, and an electric connection means for providing an electric signal to said microelectrodes and for leading out an electric signal from said microelectrodes, said electric connection means including a half-split holder which has contacts touching said electric contact points and fixes said glass plate by holding the plate at the top and bottom of the plate;

(B) a stimulation signal supply means to be connected *to* the electric connection means of said integrated cell holding instrument for providing electric stimulation to said cells; [and]

(C) *an optical observation means for observing the cells optically, and*

(*D*) a signal processing means to be connected to the electric connection means of said integrated cell holding instrument for processing an output signal arising from electric physiological activities of said cells.

[2. The cell potential measurement apparatus as in claim 1, further comprising an optical observation means for observing the cells optically.]

3. The cell potential measurement apparatus as in claim 1, further comprising a cell culturing means for maintaining an environment for culturing cells which are placed on said integrated cell holding instrument.

4. The cell potential measurement apparatus as in claim 3, wherein the cell culturing means comprises a temperature adjustment means for maintaining a constant temperature, a means for circulating a culture solution, and a means for supplying a mixed gas of air and carbon dioxide.

5. The cell potential measurement apparatus as in claim 1, wherein said plurality of microelectrodes comprise 64 electrodes arranged in 8 columns and 8 rows.

[6. The cell potential measurement apparatus as in claim 1, wherein said microelectrodes each have an electrode area of $4\times10^2$ $\mu m^2$ to $4\times10^4$ $\mu m^2$.]

7. The cell potential measurement apparatus as in claim 1, wherein said electric connection means fixes said half-split holder, and said apparatus further comprises a printed circuit board having an outside connection pattern which is connected to the contacts of said holder via a connector.

8. The cell potential measurement apparatus as in claim 1, wherein contact resistance of said electric contact points with said contacts and contact resistance of said contacts with said connector are both less than 30 m ohm.

9. The cell potential measurement apparatus as in claim 1, wherein said optical observation means comprises an optical microscope, and an image pick-up device and an image display device connected to the optical microscope.

10. The cell potential measurement apparatus as in claim 9, wherein said optical observation means further comprises an image storage device.

11. The cell potential measurement apparatus as in claim 1, wherein said stimulation signal supply means comprises a pulse signal generator.

12. The cell potential measurement apparatus as in claim 1, wherein said signal processing means comprises a multi-channel amplifier which amplifies a detection signal arising from cell activities and a multi-channel display device which displays an amplified signal waveform in real-time.

13. The cell potential measurement apparatus as in claim 1, further comprising a computer which outputs said stimulation signal via a D/A converter and receives and processes an output signal arising from electric physiological activities of said cells via an A/D converter, said computer controlling said optical observation means and said cell culturing means.

*14. A method for the continuous, simultaneous measurement of electrical physiological characteristics of at least one neural sample, comprising the steps of:*

*1.) placing said at least one neural sample on a microelectrode array of a measuring device, which device comprises:*

*(A) an integrated neural sample holding instrument provided with said microelectrode array having plurality of microelectrodes arranged in a matrix form, conductive pathways connected to said microelectrodes, a neural sample holding part which is constructed to contain at least one said neural*

*sample and an area including said plurality of microelectrodes, and said conductive pathways for providing electric stimulation signals to said microelectrodes and for leading out a responsive electric signal from said microelectrodes;*

(*B*) *a stimulation signal supply connectable to each said conductive pathways for providing electric stimulation to said neural sample; and*

(*C*) *a signal processor connectable to all of said conductive pathways of said integrated neural sample holding instrument suitable for processing said signals arising from electric physiological activities of said at least one neural sample and reflecting said signals as said complex waveforms,*

2.) *electrically stimulating at least one of said neural samples to cause an electrical response stimulus, and*

3.) *continuously simultaneously detecting said electrical response stimulus output signals arising from electric physiological activities of said neural sample and processing said signal to reflect said electrical, physiological responsive, complex waveform.*

*15. The method of claim 14 further comprising the step of maintaining an environment for culturing said neural sample on said integrated neural sample holding instrument.*

*16. The method of claim 15 further comprising the step of maintaining a constant temperature, circulating a solution, and supplying a gas supply to said neural sample holding part.*

*17. The method of claim 14 wherein said plurality of microelectrodes comprise 64 electrodes arranged in eight columns and eight rows.*

*18. The method of claim 14 wherein said microelectrodes each have an electrode area of* $4\times10^2\ \mu m^2$ *to* $4\times10^4\ \mu m^2$.

*19. The method of claim 14 wherein said electrical stimulation comprises a pulse signal.*

*20. The method of claim 14 wherein said at least one neural sample comprises a section of a nerve organ.*

*21. The method of claim 14 wherein said at least one neural sample comprises a nerve cell.*

*22. A method for the measurement of electrical, physiological response, complex waveforms in at least one neural samples, comprising the steps of*

1.) *placing at least one neural sample on a microelectrode array of a measuring device, which device comprises:*

(*A*) *an integrated, neural sample holding instrument provided with i.) said microelectrode array comprising a plurality of microelectrodes arranged in a matrix form, ii.) conductive pathways connected to the microelectrodes, and said conductive pathways for providing electric stimulation signals to said microelectrodes and for leading out an electric signal from said microelectrodes and iii.) a neural sample holding part which is constructed to contain said at least one neural sample and include said plurality of microelectrodes,*

(*B*) *a signal processor connectable to said conductive pathways of said integrated neural sample holding instrument suitable for processing said signals arising from electric physiological activities of said at least one neural sample and reflecting said signals as said complex waveforms,*

2.) *stimulating more than one of said neural samples to cause an electrical response stimulus, and*

3.) *continuously, simultaneously detecting and processing said electrical response stimulus to reflect said complex waveforms.*

*23. The method of claim 22 wherein the stimulation is an electrical signal from a stimulation signal supply connectable to all of said conductive pathways to said neural sample through said microelectrodes.*

*24. The method of claim 22 further comprising the step of maintaining an environment for culturing said neural sample on said integrated neural sample holding instrument.*

*25. The method of claim 22 further comprising the step of maintaining a constant temperature, circulating a solution, and supplying a gas supply to said neural sample holding part.*

*26. The method of claim 22 wherein said plurality of microelectrodes comprise 64 electrodes arranged in eight columns and eight rows.*

*27. The method of claim 22 wherein said microelectrodes each have an electrode area of* $4\times10^2\ \mu m^2$ *to* $4\times10^4\ \mu m^2$.

*28. The method of claim 23 wherein said electrical stimulation comprises a pulse signal.*

*29. The method of claim 22 wherein said said at least neural sample comprises a section of a nerve organ.*

*30. The method of claim 22 wherein said said at least neural sample comprises a nerve cell.*

* * * * *